United States Patent [19]
Villa et al.

[11] Patent Number: 6,100,425
[45] Date of Patent: Aug. 8, 2000

[54] PROCESS FOR THE PREPARATION OF AN INTERMEDIATE USEFUL IN THE SYNTHESIS OF IODINATED CONTRAST MEDIA

[75] Inventors: Marco Villa; Maurizio Paiocchi, both of Milan, Italy

[73] Assignee: Bracco International, B.V., Netherlands

[21] Appl. No.: 08/995,153

[22] Filed: Dec. 19, 1997

[30] Foreign Application Priority Data

Dec. 24, 1996 [IT] Italy .................................. MI96A2735

[51] Int. Cl.[7] .................................................. C07C 67/02
[52] U.S. Cl. ............................................. 560/250; 560/254
[58] Field of Search ...................................... 560/250, 254

[56] References Cited

U.S. PATENT DOCUMENTS

| | | | |
|---|---|---|---|
| 4,001,323 | 1/1977 | Felder et al. .............................. | 564/153 |
| 5,362,905 | 11/1994 | Villa et al. ................................ | 560/250 |
| 5,550,287 | 8/1996 | Cannata et al. ........................... | 564/153 |
| 5,644,010 | 7/1997 | Kurihashi et al. ....................... | 526/273 |
| 5,686,545 | 11/1997 | Kawashima et al. ................. | 526/318.4 |
| 5,686,603 | 11/1997 | Au et al. ............................. | 536/123.13 |
| 5,702,872 | 12/1997 | Imai et al. ............................... | 430/326 |

FOREIGN PATENT DOCUMENTS

| | | |
|---|---|---|
| 616 403 | 3/1980 | Switzerland . |
| 1472050 | 4/1977 | United Kingdom . |
| 2271990 | 4/1994 | United Kingdom . |
| 96/37460 | 11/1996 | WIPO . |

OTHER PUBLICATIONS

International Search Report, May 1998.

*Primary Examiner*—Samuel Barts
*Assistant Examiner*—Rosalynd Keys
*Attorney, Agent, or Firm*—Nixon & Vanderhye P.C.

[57] ABSTRACT

A process for the preparation of the compound L-5-(2-acetoxypropionylamino)-2,4,6-triiodoisophthaloyl dichloride by reacting 5-amino-2,4,6-triiodoisophthaloyl dichloride with L-2-acetoxypropionyl chloride in N,N-dimethylacetamide as a solvent, characterized in that a catalytic amount of a lower alcohol is added to the reaction mixture.

4 Claims, No Drawings

PROCESS FOR THE PREPARATION OF AN INTERMEDIATE USEFUL IN THE SYNTHESIS OF IODINATED CONTRAST MEDIA

The present invention relates to a process for the preparation of an intermediate useful in the synthesis of iodinated contrast media, more particularly, to a process for the preparation of the compound L-5-(2-acetoxypropionylamino)-2,4,6-triiodo-isophthaloyl dichloride (hereinafter referred to as compound A). Compound A, disclosed in British Patent n° 1,472,050 (Savac AG), is an intermediate for the synthesis of (S)-N,N'-bis[2-hydroxy-(1-hydroxymethyl)ethyl]-5-(2-hydroxy-propionylamino)-2,4,6-triiodo-isophthalamide, an X-ray non-ionic contrast medium, also known under the international non-proprietary name Iopamidol.

The preparation of compound A as disclosed in the above cited British Patent (example 1b) is performed adding L-2-acetoxypropionyl chloride to a solution of 5-amino-2,4,6-triiodo-isophthaloyl dichloride in N,N-dimethylacetamide at 3°–50° C. according to the following scheme.

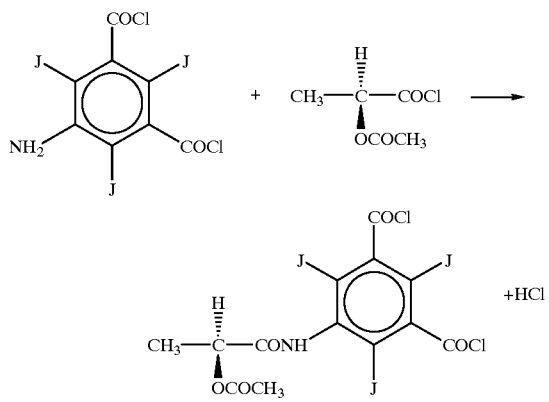

The reaction described in example 1b of British Patent n° 1,472,050 has some drawbacks—in particular a partial racemization of L-2-acetoxypropionyl chloride—which make it industrially unsuitable. In this connection, it should be stressed that through the reaction between 5-amino-2,4,6-triiodo-isophthaloyl dichloride and L-2-acetoxypropionyl chloride the stereogenic center present in the Iopamidol molecule is inserted. The purity requirements of Iopamidol as an X-ray contrast medium involve of course also the optical purity of the compound itself (specific rotatory power from −4.6° to −5.2°, reported in the "Farmacopea Ufficiale della Repubblica Italiana", (Italian Official Pharmacopoeia, Ninth edition, II Supplement, 1991, page 429, corresponding to an e. e. $\geq$89%.

Therefore it is of paramount importance that, starting from the reaction for the preparation of compound A, the enantiomeric purity of the various synthetic intermediates be maintained high in order to avoid the need for a purification of the final product from the undesired enantiomer. To this purpose, the reaction for the preparation of compound A makes use of L-2-acetoxypropionyl chloride with a high enantiomeric purity, generally with an e. e. $\geq$95%, preferably higher than 97%.

Improvements to the process described above have been recently reported in literature, which involve the addition of catalytic amounts of acids to the reaction mixture. In particular, the addition of catalytic amounts of Lewis acids has been described in British Patent application n° 2,271,990 in the Applicant's name, while the addition of catalytic amounts of halo acids has been described in International Patent application n. WO 96/37460 in the name of Fructamine S.p.a.

Now it has been found that the same improvements can be attained in the preparation of compound A, mainly as far as the reduction in the racemization of L-2-acetoxypropionyl chloride is concerned, while avoiding the addition of some acids to the reaction mixture.

It is therefore the object of the present invention a process for the preparation of L-5-(2-acetoxypropionylamino)-2,4,6-triiodo-isophthaloyl dichloride by reaction of 5-amino-2,4,6-triiodo-isophthaloyl dichloride with L-2-acetoxypropionyl chloride in N,N-dimethylacetamide as a solvent, in which process a catalytic amount of a lower alcohol is added to the reaction mixture.

The improved process of the present invention allows to obtain compound A with a high enantiomeric purity, i.e. with an e. e. higher than 92%. Racemization is thus minimized and the resulting compound A has an enantiomeric purity degree suitable for using it directly as a crude in the synthesis of Iopamidol, thus obtaining Iopamidol with a rotatory power fulfilling the requirements of Pharmacopoeia. "Lower alcohol" means an alcohol selected from methanol, ethanol, propanol, isopropanol, n-butanol, sec-butanol, isobutanol and tert-butanol. Preferably, the lower alcohol is methanol or ethanol. The lower alcohol is added in catalytic amounts. "Catalytic amounts" generally means an amount lower than stoichiometric, i.e. lower than a 1:1 molar ratio on the basis of the starting products. In practice, since the reaction between L-2-acetoxypropionyl chloride and 5-amino-2,4,6-triiodoisophthaloyl dichloride is carried out using an L-2-acetoxypropionyl chloride excess, the catalytic amount of lower alcohol is meant on the basis of 5-amino-2,4,6-triiodoisophthaloyl dichloride.

Preferably the amount of lower alcohol used in the process of the present invention ranges from 5% to 50% by mole per mole of 5-amino-2,4,6-triiodoisophthaloyl dichloride. Most preferably, the amount of lower alcohol ranges from 10% to 30% by mole per mole of 5-amino-2,4,6-triiodoisophthaloyl dichloride.

The lower alcohol is preferably added to the solution of L-2-acetoxypropionyl chloride in N,N-dimethylacetamide before the addition of the 5-amino-2,4,6-triiodo-isophthaloyl dichloride. The reaction temperature is generally low, preferably from 0° C. to 25° C. Temperature is not a critical parameter. However, operating at lower temperatures, racemization is further limited but the reaction rate is lower. On the contrary, when operating at too high temperatures, racemization is liable to increase.

Although the process of the invention is illustrated with particular reference to N,N-dimethylacetamide as the solvent, the process can be carried out similarly in other dipolar aprotic solvents such as N-methyl-2-pyrrolidone.

As already noted, the process of the invention minimizes racemization to values which allow to obtain compound A with an enantiomeric purity degree suitable for the preparation of Iopamidol fulfilling the requirements of Pharmacopoeia, without need for further purifications.

A preferred embodiment of the process of the invention is described in the following. A catalytic amount of methanol is added to a solution of L-2-acetoxypropionyl chloride in N,N-dimethylacetamide, then 5-amino-2,4,6-triiodo-isophthaloyl dichloride is added thereto. After that, the mixture is kept at room temperature for about 12–16 hours. The reaction mixture is treated with cellosolve and water to obtain a precipitate which is filtered, washed and dried to obtain compound A with an enantiomeric purity substantially corresponding to that of the starting L-2-acetoxypropionyl chloride.

A further object of the invention is a process for the preparation of Iopamidol, characterized in that the intermediate L-5-(2-acetoxypropionylamino)-2,4,6-triiodoisophthaloyl dichloride is obtained by reacting 5-amino-2,4,6-triiodoisophthaloyl dichloride with L-2-acetoxypropionyl chloride in the presence of N,N-dimethylacetamide as the solvent, adding a catalytic amount of a lower alcohol to the reaction mixture. Using this intermediate Iopamidol is prepared as described in British Patent 1,472,050.

The present invention is further illustrated by the following examples.

EXAMPLE 1

A 250 ml round-bottomed flask, fitted with mechanical stirring and kept under inert atmosphere, is loaded with N,N-dimethylacetamide (30 ml), then cooled at −2°–0° C. and L-2-acetoxypropionyl chloride (20 g; 0.133 moles; e. e. 97.4%) is added drop by drop in an hour. When the addition is completed, methanol (0.215 g; 6.7 mmoles) is added. Temperature is adjusted to 12° C. and a solution of N,N-dimethylacetamide (30 ml) and 5-amino-2,4,6-triiodoisophthaloyl dichloride (40 g; 67 mmoles) is dropped therein in 6 hours. After that, the solution is warmed to 19°–20° C., keeping this temperature for 14–16 hours. The mixture is cooled to 5°–10° C. and cellosolve (40 ml) is added, keeping temperature lower than 20° C. The solution is added drop by drop to water (280 ml) in about 1 hour, keeping temperature at 15°–20° C. The suspension is stirred for 30 minutes and the precipitate is filtered, washed with water (2×30 ml) and dried under vacuum at 50° C. until constant weight to obtain 42.5 g of the desired product. Titre ≧97%, 93.6% e. e., 89% yield.

EXAMPLE 2

A 250 ml round-bottomed flask, fitted with mechanical stirring and kept under inert atmosphere, is loaded with N,N-dimethylacetamide (60 ml), then cooled at −2°–0° C. and L-2-acetoxypropionyl chloride (20 g; 0.133 moles; e. e. 97.4%) is added drop by drop in an hour. When the addition is completed, methanol (0.645 g; 20.1 mmoles) is added. Temperature is adjusted to 12° C. and a 5-amino-2,4,6-triiodoisophthaloyl dichloride (40 g; 67 mmoles) is added in 6 equal portions, one per hour. After that, the solution is warmed to 19°–20° C., keeping this temperature for 14–16 hours. The mixture is cooled to 5°–10° C. and cellosolve (40 ml) is added, keeping temperature lower than 20° C. The solution is added drop by drop to water (280 ml) in about 1 hour, keeping temperature at 15°–20° C. The suspension is stirred for 30 minutes and the precipitate is filtered, washed with water (2×30 ml) and dried under vacuum at 50° C. until constant weight to obtain 43 g of the desired product. Titre ≧97%, 94.8% e. e., 90% yield.

What is claimed is:

1. A process for the preparation of L-5-(2-acetoxypropionylamino)-2,4,6-triiodo-isophthaloyl dichloride by reacting 5-amino-2,4,6-triiodoisophthaloyl dichloride with L-2-acetoxypropionyl chloride in N,N-dimethylacetamide as the solvent comprising conducting the reaction in the presence of from 5% to 50% by mole per mole of 5-amino-2,4,6-triiodoisophthaloyl dichloride.

2. A process according to claim 1 wherein the lower alcohol is selected from methanol, ethanol, propanol, isopropanol, n-butanol, sec-butanol, isobutanol and tert-butanol.

3. A process according to claim 2 wherein the lower alcohol is methanol or ethanol.

4. A process according to claim 1 wherein the amount of lower alcohol ranges from 10% to 30% per mole of 5-amino-2,4,6-triiodoisophthaloyl dichloride.

* * * * *